United States Patent
Kato et al.

(10) Patent No.: US 9,901,547 B2
(45) Date of Patent: Feb. 27, 2018

(54) SOFT CAPSULE SHELL

(71) Applicant: FUJI CAPSULE CO., LTD., Fujinomiya-shi (JP)

(72) Inventors: Kenji Kato, Fujinomiya (JP); Kazuhiko Watanabe, Fujinomiya (JP); Takashi Inoue, Fuji (JP); Yosuke Kondo, Fujinomiya (JP)

(73) Assignee: FUJI CAPSULE CO., LTD., Fujinomiya-shi (JP)

( * ) Notice: Subject to any disclaimer, the term of this patent is extended or adjusted under 35 U.S.C. 154(b) by 120 days.

(21) Appl. No.: 14/904,977

(22) PCT Filed: Jul. 15, 2014

(86) PCT No.: PCT/JP2014/068787
§ 371 (c)(1),
(2) Date: Jan. 14, 2016

(87) PCT Pub. No.: WO2015/008748
PCT Pub. Date: Jan. 22, 2015

(65) Prior Publication Data
US 2016/0175258 A1    Jun. 23, 2016

(30) Foreign Application Priority Data

Jul. 18, 2013   (JP) .................................. 2013-149040
Sep. 24, 2013   (WO) ....................... PCT/JP13/75728

(51) Int. Cl.
| | |
|---|---|
| A61K 8/02 | (2006.01) |
| A61K 8/73 | (2006.01) |
| A61K 9/48 | (2006.01) |
| A23P 10/30 | (2016.01) |
| A23L 29/256 | (2016.01) |

(52) U.S. Cl.
CPC .......... *A61K 9/4816* (2013.01); *A23L 29/256* (2016.08); *A23P 10/30* (2016.08); *A61K 8/02* (2013.01); *A61K 8/73* (2013.01); *A61K 8/732* (2013.01); *A61K 9/4891* (2013.01); *A23V 2002/00* (2013.01); *A61K 2800/82* (2013.01)

(58) Field of Classification Search
CPC ......... A23L 29/256; A23P 10/30; A61K 8/02; A61K 8/73; A61K 8/732; A61K 9/4816; A61K 9/4891; A61K 2800/82; A23V 2002/00
See application file for complete search history.

(56) References Cited

U.S. PATENT DOCUMENTS

| | | |
|---|---|---|
| 39,079 A | 6/1863 | Teale |
| 6,340,473 B1 | 1/2002 | Tanner et al. |
| 6,582,727 B2 | 6/2003 | Tanner et al. |
| 2002/0081331 A1 | 6/2002 | Tanner et al. |
| 2003/0138482 A1 | 7/2003 | Fonkwe et al. |

FOREIGN PATENT DOCUMENTS

| | | | |
|---|---|---|---|
| JP | 2003-504326 A | | 2/2003 |
| JP | 2006-096695 A | | 4/2006 |
| JP | 2006231219 | * | 9/2006 |
| JP | 2008-237572 A | | 10/2008 |
| JP | 2009-173607 A | | 8/2009 |
| JP | 2010-180159 A | | 8/2010 |
| JP | 2011-026262 A | | 2/2011 |
| KR | 10-0541722 B1 | | 1/2006 |
| WO | 2001/003677 A1 | | 1/2001 |

OTHER PUBLICATIONS

International Search Report dated Sep. 22, 2014 for PCT/JP2014/068787 filed on Jul. 15, 2014.
Extended European Search Report dated Feb. 16, 2017 in Patent Application No. 14825991.4.

* cited by examiner

*Primary Examiner* — Irina S Zemel
(74) *Attorney, Agent, or Firm* — Oblon, McClelland, Maier & Neustadt, L.L.P.

(57) ABSTRACT

Provided are a plant-derived soft capsule shell having a high shell sheet strength, a good adhesive property, and excellent shell performance, and a soft capsule. The soft capsule shell comprises: (A) iota carrageenan; and (B) a starch dispersion obtained by ultrasonically treating a starch paste solution.

16 Claims, No Drawings

SOFT CAPSULE SHELL

TECHNICAL FIELD

The present invention relates to a soft capsule shell and a soft capsule using the same.

BACKGROUND ART

Soft capsules are used in a wide range of fields including pharmaceuticals, foods, and cosmetics. The most popular shell base for the soft capsules is gelatin, and gelatin is inexpensive and non-toxic and exhibits an excellent mechanical strength, shell-forming ability, and the like.

On the other hand, because of a recent problem of bovine spongiform encephalopathy (BSE) or for religious reasons, an alternative to animal-derived gelatin has been required, and capsules are no exception.

In view of the foregoing, a variety of investigations have been made on a capsule shell using a plant-derived base, and there have been previously reported, for example, a capsule shell including processed starch obtained by subjecting waxy corn starch to acid treatment and iota carrageenan (Patent Literature 1), a film-forming composition for a soft capsule including acid-decomposed waxy corn starch, a gelling agent, and a plasticizer (Patent Literature 2), a soft capsule outer shell formed by blending starch, A-carrageenan, a metal salt, dextrin, a plasticizer, and water (Patent Literature 3), and a soft capsule outer shell formed by blending a starch derivative mixture, a starch decomposed matter, a gum mix, reduced maltose, a plasticizer, and water (Patent Literature 4).

CITATION LIST

Patent Literature

[PTL 1] JP-A-2011-26262
[PTL 2] JP-A-2010-180159
[PTL 3] JP-A-2008-237572
[PTL 4] JP-A-2006-96695

SUMMARY OF INVENTION

Technical Problem

In general, the soft capsule shell is required to have appropriate fluidity of a shell solution during capsule production, a good film-forming property, an appropriate shell sheet strength, elongation, and adhesive property, and the like. Further, after capsulation, the capsule is required to have blocking resistance for preventing adhesion of the capsules, elasticity, transparency, disintegrability, and the like.

However, the shells of the related-art described above are actually far from having such shell performance comprehensively. In particular, the shell having a conventional shell composition and having the same shell sheet thickness as a common gelatin shell (about 0.9 mm) is insufficient in shell sheet strength and adhesive force in many cases. Therefore, the shell sheet strength and adhesive force required for capsulation have been ensured by thinning a shell sheet (about 0.6 mm). However, when particles in a content solution enter a contact portion of a shell prepared from a thinned shell sheet, a tiny hole is opened at the contact portion and thereby sometimes causes a problem in that a capsule content is leaked out. This problem significantly arises as the shell sheet is thinner.

The present invention was made in view of the above-mentioned circumstances and relates to providing a plant-derived soft capsule shell having a high shell sheet strength, a good adhesive property, and excellent shell performance, and a soft capsule.

Solution to Problem

The inventors of the present invention made various investigations to solve the above-mentioned problems, and as a result, found that a combination of iota carrageenan and a specific starch dispersion obtained by ultrasonically treating a starch paste solution provided a capsule shell exhibiting a high shell sheet strength and a good adhesive property while suppressing enter into a contact portion of a shell base. Further, the inventors found that after capsulation, the shell had excellent shell performance, such as blocking resistance, elasticity, transparency, and rapid disintegrability, and completed the present invention.

That is, according to one embodiment of the present invention, provided is a soft capsule shell, comprising: (A) iota carrageenan; and (B) a starch dispersion obtained by ultrasonically treating a starch paste solution.

According to another embodiment of the present invention, provided is a soft capsule, which is produced by using the soft capsule shell.

Advantageous Effects of Invention

According to the embodiments of the present invention, a soft capsule that suppresses the content of the capsule from leaking out without use of animal-derived gelatin can be provided. The soft capsule according to the embodiment of the present invention is also excellent in shell performance, such as blocking resistance, elasticity, transparency, and disintegrability after drying.

DESCRIPTION OF EMBODIMENTS

The soft capsule shell of the present invention comprises: (A) iota carrageenan; and (B) a starch dispersion obtained by ultrasonically treating a starch paste solution.

Carrageenan is a kind of galactan having a sulfate group and is known to be present in red algae. According to the regulation of food additives in Japan, three kinds of carrageenans including "purified carrageenan", "semirefined carrageenan", and "powered red algae" are specified (see "Annotation book of list of existing food additives" (1999), published by Japan Food Additives Association), but all of them are essentially included in the carrageenan to be used in the present invention, as the carrageenans differ only in purification degrees.

The carrageenans may be pure products or may contain a standardizing agent. In this context, examples of the standardizing agent include one or more kinds selected from the group consisting of: sugars, such as sucrose, glucose, maltose, and lactose; and dextrin. In the case where the carrageenan contains a standardizing agent, the ratio of the standardizing agent is preferably 50 mass % or less, more preferably 45 mass % or less. It should be noted that in the case of utilizing the carrageenan containing a standardizing agent, the standardizing agent is included in the content of carrageenan to be described later. The carrageenan may be mainly classified into three kinds including iota carrageenan, kappa carrageenan, and lambda carrageenan with respect to differences in gelation characteristic and structure. In the present invention, iota carrageenan is used as a component (A).

The content of (A) the iota carrageenan is preferably 20 mass % or more, more preferably 25 mass % or more, more preferably 30 mass % or more, even more preferably 35 mass % with respect to the total amount of solid components in view of a shell sheet strength and elasticity. Further, the content is preferably 55 mass % or less, more preferably 50 mass %, even more preferably 45 mass % or less with respect to the total amount of the solid components in view of a shell solution viscosity. Further, the content of (A) the iota carrageenan is preferably from 20 mass % to 55 mass %, more preferably from 25 mass % to 55 mass %, more preferably from 30 mass % to 50 mass %, even more preferably from 35 mass % to 45 mass % with respect to the total amount of the solid components. It should be noted that in the present invention, the solid components mean components excluding purified water and a plasticizer from the shell composition.

(B) The starch dispersion obtained by ultrasonically treating a starch paste solution to be used in the present invention is a known substance and is produced from starch by the method disclosed in JP-B2-4288381 or a method equivalent thereto.

The starch paste solution is prepared by an ordinary method, for example, by heating starch in water or the like to gelatinize starch matter. The content of the starch in the starch paste solution is not particularly limited but is preferably 1 mass % or more, more preferably 5 mass % or more, even more preferably 10 mass % or more.

As the kind of the starch, there are given, for example, corn starch, waxy corn starch, tapioca starch, potato starch, sweet potato starch, and wheat starch. One kind of those starches may be used alone, or two or more kinds thereof may be used in combination. Of those, waxy corn starch is preferred from a comprehensive viewpoint (in view of a shell strength and a gelation strength).

It should be noted that the starch to be used in preparation of the starch paste solution is preferably a chemically unmodified starch, i.e., starch not subjected to chemical modification, such as acid treatment, pregelatinization, etherification, and acetylation.

Further, the viscosity of the starch paste solution in the ultrasonic treatment (B-type viscometer, starch content of 5 mass %, liquid temperature of 95° C.) varies depending on the kind of the starch, but is preferably from 400 mPa·s to 800 mPa·s, more preferably from 400 mPa·s to 600 mPa·s.

The conditions of the ultrasonic treatment may be appropriately set.

The starch paste solution is reduced in viscosity to provide a starch dispersion through the ultrasonic treatment. The viscosity of the starch dispersion after the ultrasonic treatment (B-type viscometer, starch content of 20 mass %, liquid temperature of 80° C.) varies depending on the kind of the starch, but is preferably 350 mPa·s or less, more preferably from 10 mPa·s to 350 mPa·s.

(B) The starch dispersion obtained by ultrasonically treating a starch paste solution may be in a liquid form and is preferably in a dried form obtained by drying the dispersion in a liquid form. As a drying method, there are given, for example, spray drying, freeze drying, and evaporation to dryness.

In the present invention, a commercially available product may also be used as (B) the starch dispersion obtained by ultrasonically treating a starch paste solution.

The content of (B) the starch dispersion obtained by ultrasonically treating a starch paste solution (dry mass, the same applies hereinafter) is preferably 10 mass % or more, more preferably 20 mass % or more, more preferably 28 mass % or more, more preferably 35 mass % or more, more preferably 45 mass % or more, more preferably 50 mass % or more, even more preferably 55 mass % or more with respect to the total amount of the solid components in view of an adhesive property. Further, the content is preferably 75 mass % or less, more preferably 70 mass % or less, even more preferably 65 mass % or less with respect to the total amount of the solid components in view of a shell sheet strength. Further, the content of (B) the starch dispersion obtained by ultrasonically treating a starch paste solution is preferably from 10 mass % to 75 mass %, more preferably from 20 mass % to 75 mass %, more preferably from 28 mass % to 75 mass %, more preferably from 45 mass % to 75 mass %, more preferably from 50 mass % to 70 mass %, even more preferably from 55 mass % to 65 mass % with respect to the total amount of the solid components.

In the present invention, the content mass ratio [(A):(B)] between (A) the iota carrageenan and (B) the starch dispersion obtained by ultrasonically treating a starch paste solution with respect to the total amount of the solid components is preferably from 1:0.3 to 1:3, more preferably from 1:0.6 to 1:2.5, even more preferably from 1:1 to 1:2.3 from a comprehensive viewpoint (in view of a shell strength and a gelation strength).

The soft capsule shell of the present invention preferably further comprises kappa carrageenan in view of gelation promotion.

The content of the kappa carrageenan is preferably 0.1 mass % or more, more preferably 0.3 mass % or more, even more preferably 0.5 mass % or more with respect to the total amount of the solid components in view of a gelation strength. Further, the content is preferably 3.5 mass % or less, more preferably 2.5 mass % or less in view of a shell strength (fragility). The content of the kappa carrageenan is preferably from 0.1 mass % to 3.5 mass %, more preferably from 0.3 mass % to 3.5 mass %, even more preferably from 0.5 mass % to 2.5 mass % with respect to the total amount of the solid components.

A gelling agent other than the iota or kappa carrageenan, such as sodium alginate, pullulan, glucomannan, gum arabic, or furcellaran, may be incorporated into the soft capsule shell of the present invention as required.

However, the content of the gelling agent other than the iota or kappa carrageenan is preferably 1 mass % or less, more preferably 0.5 mass % or less, even more preferably 0.1 mass % or less with respect to the total amount of the solid components in view of physical properties of the shell and quality of a soft capsule.

Further, starches other than the starch dispersion obtained by ultrasonically treating a starch paste solution, such as unmodified starch, chemically modified starch, and a degraded starch, may be incorporated into the soft capsule shell of the present invention as required.

The content of the starches other than the starch dispersion obtained by ultrasonically treating a starch paste solution is preferably 50 mass % or less, more preferably 47 mass % or less, more preferably 45 mass % or less, even more preferably 10 mass % or less with respect to the total amount of the solid components in view of a shell sheet strength, an adhesive force, and elasticity after drying. The lower limit is 0 mass %.

Further, various additives to be used for a soft capsule shell, such as a plasticizer, a natural pigment, a synthetic pigment, various sweeteners, an antiseptic, a water activity reducing agent, and a pH adjustor, may be further incorporated into the soft capsule shell of the present invention as required.

The plasticizer is not particularly limited, and examples thereof include glycerin, sorbitol, erythritol, propylene glycol, and polyethylene glycol. Of those, glycerin or sorbitol is preferred.

The content of the plasticizer in the soft capsule shell of the present invention is preferably 30 parts by mass or more, more preferably 35 parts by mass or more with respect to 100 parts by mass of the total amount of the solid components in view of flexibility. Further, the content is preferably 60 parts by mass or less, more preferably 50 parts by mass or less with respect to 100 parts by mass of the total amount of the solid components in view of adhesiveness. The content of the plasticizer is preferably from 30 parts by mass to 60 parts by mass, more preferably from 35 parts by mass to 50 parts by mass with respect to 100 parts by mass of the total amount of the solid components.

The soft capsule shell of the present invention may be produced according to an ordinary method. For example, it is only necessary that (A) the iota carrageenan and (B) the starch dispersion obtained by ultrasonically treating a starch paste solution, and as required, various additives be stirred and dispersed in water, and the resultant be stirred and dissolved at from 70° C. to 98° C., followed by vacuum defoaming.

Water is added in an amount of preferably 160 parts by mass or more, more preferably 200 parts by mass or more with respect to 100 parts by mass of the total amount of the solid components. When a large amount of water is contained in the shell solution, the thickness of the shell after drying is rather thinner and therefore, effects such as easy swallowing and rapid disintegration are achieved.

A soft capsule is obtained by molding such soft capsule shell into a predetermined shape, followed by drying. The soft capsule may be produced, for example, by a conventionally used production method for a soft capsule, such as a punching method using a rotary die-type soft capsule filling machine or the like, or a flat plate method. Of those, from the viewpoints of effectively exhibiting the effects of the present invention, and industrial productivity, the soft capsule is preferably produced by a rotary die system. The rotary die-type soft capsule filling machine is used in a method involving punching two shell sheets formed by spreading the soft capsule shell solution on a rotary drum into a capsule shape by a pair of rotating dies (die rolls) and can simultaneously perform forming a soft capsule and filling the capsule with a capsule content.

The shape of the soft capsule is not particularly limited and examples thereof include an oval (football) type, an oblong (long ellipse) type, a round (spherical) type, a tube type, and special shape such as a self-cut type. It should be noted that the "self-cut type" includes a hollow body having a content encapsulated therein and a tab connected to the top end of the body via a neck portion, and is used by twisting the tab off from the body to leak out a drug, a cosmetic, a food, a chemical, or the like encapsulated in the body. The self-cut type is sometimes referred to as "twist-off" or "wrench-off type".

The soft capsule of the present invention may be utilized in a variety of applications such as pharmaceuticals, quasi-drugs, cosmetics, and foods, and the composition of the capsule content is appropriately determined depending on the applications. The form of the content may be a solution, a suspension, a paste, a powder, a granule, or the like.

Components that may be contained in the capsule are exemplified below. The components may be contained in any portion of the capsule.

As an oil and fat, the capsule may contain, for example, an avocado oil, an almond oil, a linseed oil, a fennel oil, a perilla oil, an olive oil, olive squalene, an orange oil, an orange roughy oil, a sesami oil, a garlic oil, cacao butter, a pumpkin seed oil, a chamomile oil, a carrot oil, a cucumber oil, a beef tallow fatty acid, a kukui nut oil, a cranberry seed oil, a brown rice germ oil, a rice oil, a wheat germ oil, a safflower oil, shea butter, liquid shea butter, a perilla oil, a soybean oil, an evening primrose oil, a camellia oil, a corn oil, a rapeseed oil, a saw palmetto extract oil, a Job's tears speed oil, a persic oil, a parsley seed oil, a castor oil, a sunflower oil, a grape seed oil, a borage oil, a macadamia nut oil, a meadowfoam oil, a cottonseed oil, a peanut oil, a turtle oil, a mink oil, an egg-yolk oil, a fish oil, a palm oil, a palm kernel oil, Japan wax, a coconut oil, long-chain, medium-chain, and short-chain fatty acid triglycerides, diacylglycerides, beef tallow, lard, squalene, squalane, pristane, and hydrogenated products of these oils and fats.

As a wax, the capsule may contain, for example, shellac wax, beeswax, carnauba wax, spermaceti, lanolin, liquid lanolin, reduced lanolin, hard lanolin, cyclic lanolin, lanolin wax, candelilla wax, Japan wax, montan wax, shellac wax, and rice wax. As a hydrogenated oil, the capsule may contain, for example, a hydrogenated vegetable oil obtained by hydrogenating a vegetable oil and fat, hydrogenated beef tallow, and hydrogenated lard.

As a mineral oil, the capsule may contain, for example, liquid paraffin, vaseline, paraffin, ozokerite, ceresin, and microcrystalline wax.

As a fatty acid, the capsule may contain, for example: a natural fatty acid, such as lauric acid, myristic acid, palmitic acid, stearic acid, behenic acid, oleic acid, linoleic acid, conjugated linoleic acid, linolenic acid, docosahexaenoic acid, eicosapentaenoic acid, 12-hydroxystearic acid, undecylenic acid, tall oil, or lanolin fatty acid; a synthetic fatty acid, such as isononanoic acid, caproic acid, 2-ethylbutanoic acid, isopentanoic acid, 2-methylpentanoic acid, 2-ethylhexanoic acid, or isopentanoic acid; and oils and fats containing these fatty acids as fatty acid compositions.

As a vitamin, the capsule may contain, for example: vitamin A family: retinol, retinal (vitamin A1), dehydroretinal (vitamin A2), carotene, and lycopene (provitamin A); vitamin B family: fursultiamine, thiamine hydrochloride, and thiamine sulfate (vitamin B1), riboflavin (vitamin B2), pyridoxine (vitamin B6), cyanocobalamin, methylcobalamin (vitamin B12), a folic acid, a nicotinic acid, a pantothenic acid, a biotin, choline, and an inositol; vitamin C family: ascorbic acid or a derivative thereof; vitamin D family: ergocalciferol (vitamin D2), cholecalciferol (vitamin D3), and dihydrotachysterol; vitamin E family: vitamin E or a derivative thereof; a ubiquinone; vitamin K family: phytonadione (vitamin K1), menaquinone (vitamin K2), menatetrenone, menadione (vitamin K3), and menadiol (vitamin K4) as well as an essential fatty acid (vitamin F), carnitine, ferulic acid, γ-oryzanol, orotic acid, a vitamin P (rutin, eriocitrin, or hesperidin), and vitamin U.

As a stimulant, the capsule may contain, for example, a capsicum tincture, a capsicum oil, nonylic acid vanillylamide, a cantharides tincture, a ginger tincture, a ginger oil, a mint oil, 1-menthol, camphor, and benzyl nicotinate.

As a UV absorbing or shielding agent, the capsule may contain, for example, a benzophenone derivative (such as 2-hydroxy-4-methoxybenzophenone, 2-hydroxy-4-methoxybenzophenone-5-sulfonic acid, sodium 2-hydroxy- 4-methoxybenzophenone-5-sulfonate, dihydroxydimethoxybenzophenone, sodium dihydroxydimethoxybenzophenone-sulfonate, 2,4-dihydroxybenzophenone, or tetrahydroxybenzophenone), a p-aminobenzoic acid derivative (such as p-aminobenzoic acid, ethyl p-aminobenzoate, glyceryl p-aminobenzoate, amyl p-dimethylaminobenzoate, or octyl p-dimethylaminobenzoate), a methoxycinnamic acid derivative (such as ethyl p-methoxycinnamate, isopropyl p-methoxycinnamate, octyl p-methoxycinnamate, 2-ethoxyethyl p-methoxycinnamate, sodium p-methoxycinnamate, potassium p-methoxycinnamate, or glyceryl di-p-methoxycinnamate mono-2-ethylhexanoate), a salicylic acid derivative (such as octyl salicylate, phenyl salicylate, homomenthyl salicylate, dipropylene glycol salicylate, ethylene glycol salicylate, myristyl salicylate, or methyl salicylate), an anthranilic acid derivative (such as methyl anthranilate), a urocanic acid derivative (such as urocanic acid or ethyl urocanate), a coumarin derivative, an amino acid compound, a benzotriazole derivative, a tetrazole derivative, an imidazoline derivative, a pyrimidine derivative, a dioxane derivative, a camphor derivative, a furan derivative, a pyrone derivative, a nucleic acid derivative, an allantoin derivative, a nicotinic acid derivative, a vitamin B6 derivative, umbelliferone, esculin, benzyl cinnamate, cinoxate, oxybenzone, dioxybenzone, octabenzone, sulisobenzone, benzoresorcinol, arbutin, guaiazulene, shikonin, baicalin, baicalein, berberine, Neo Heliopan, Escalol, zinc oxide, talc, and kaolin.

As a whitening agent, the capsule may contain, for example, a p-aminobenzoic acid derivative, a salicylic acid derivative, an anthranilic acid derivative, a coumarin derivative, an amino acid compound, a benzotriazole derivative, a tetrazole derivative, an imidazoline derivative, a pyrimidine derivative, a dioxane derivative, a camphor derivative, a furan derivative, a pyrone derivative, a nucleic acid derivative, an allantoin derivative, a nicotinic acid derivative, vitamin C or a derivative thereof (such as a magnesium salt of vitamin C phosphate or vitamin C glucoside), vitamin E or a derivative thereof, kojic acid or a derivative thereof, oxybenzone, benzophenone, arbutin, guaiazulene, shikonin, baicalin, baicalein, berberine, a placenta extract, ellagic acid, and Rucinol.

As a tyrosinase activity inhibitor, the capsule may contain, for example, vitamin C or a derivative thereof (such as a magnesium salt of vitamin C phosphate or vitamin C glucoside), hydroquinone or a derivative thereof (such as hydroquinone benzyl ether), kojic acid or a derivative thereof, vitamin E or a derivative thereof, N-acetyltyrosine or a derivative thereof, glutathione, hydrogen peroxide, zinc peroxide, a placenta extract, ellagic acid, arbutin, Rucinol, a silk extract, and a plant extract (chamomile, mulberry, common gardenia, Japanese angelica root, burnet, shrubby sophora, mugwort, Japanese honeysuckle, phellodendron bark, *Houttuynia cordata, Wolfiporia extensa*, Job's tears, white dead nettle, hop, crataegus fruit, eucalyptus, yarrow, *Althaea Officinalis*, cinnamon, vitex rotundifolia fruit, hamamelis, white mulberry or Japanese mulberry, isodon herb, platycodon root, dodder seed, Euphorbia lathyris seed, leopard flower, ephedra herb, cnidium rhizome, aralia rhizome, bupleurum root, *Saposhnikovia*, American silvertop, scutellaria root, moutan bark, peony root, *Geranium*, puararia root, glycyrrhiza, sumac gallnut, aloe, cimicifuga rhizome, safflower, green tea, black tea, or gambir).

As a melanin pigment reducing or decomposing substance, the capsule may contain, for example, phenylmercuric hexachlorophene, mercuric oxide, mercurous chloride, hydrogen peroxide water, zinc peroxide, and hydroquinone or a derivative thereof.

As a substance for accelerating turnover or activating cells, the capsule may contain, for example, hydroquinone, an extract of lactic acid bacteria, a placenta extract, a reishi mushroom extract, vitamin A, vitamin E, allantoin, a spleen extract, a thymus extract, a yeast extract, a fermented milk extract, and a plant extract (aloe, scutellaria root, horsetail, gentian, burdock, lithospermum root, carrot, hamamelis, hop, coix seed, white dead nettle, *Swertia japonica*, Japanese angelica root, pot marigold, sweet hydrangea leaf, *Hypericum erectum*, cucumber, thyme, rosemary, or parsley).

As an astringent, the capsule may contain, for example, succinic acid, allantoin, zinc chloride, zinc sulfate, zinc oxide, calamine, zinc p-phenolsulfonate, aluminum potassium sulfate, resorcin, ferric chloride, and tannic acid (including a cathechin compound).

As an active oxygen scavenger, the capsule may contain, for example, SOD, catalase, and glutathione peroxidase.

As an antioxidant, the capsule may contain, for example, vitamin C or a salt thereof, a stearic acid ester, vitamin E or a derivative thereof, nordihydroguaiaretic acid, butylhydroxytoluene (BHT), butylhydroxyanisole (BHA), hydroxytyrosol, p-hydroxyanisole, propyl gallate, sesamol, sesamolin, gossypol, and propolis.

As a lipid peroxide formation suppressing agent, the capsule may contain, for example, β-carotene and a plant extract (such as cultured cells of sesame, sweet hydrangea leaf, *Hypericum erectum*, hamamelis, clove, melissa, isodon herb, white birch, scarlet sage, rosemary, a fruit of heavenly bamboo, rose fruit, ginkgo, or green tea).

As an anti-inflammatory agent, the capsule may contain, for example, ichthammol, indomethacin, kaolin, salicylic acid, sodium salicylate, methyl salicylate, acetylsalicylic acid, diphenhydramine hydrochloride, d-camphor, dl-camphor, hydrocortisone, guaiazulene, chamazulene, chlorpheniramine maleate, glycyrrhizic acid or a salt thereof, glycyrrhetinic acid or a salt thereof, a glycyrrhiza extract, a lithospermum root extract, a rose fruit extract, and propolis.

As an antibacterial, sterilizing, or disinfecting agent, the capsule may contain, for example, acrinol, sulfur, calcium gluconate, chlorhexidine gluconate, sulfamine, mercurochrome, lactoferrin or a hydrolysate thereof, an alkyl diaminoethyl glycine chloride liquid, triclosan, sodium hypochlorite, chloramine T, bleaching powder, an iodine compound, iodoform, sorbic acid or a salt thereof, propionic acid or a salt thereof, salicylic acid, dehydroacetic acid, a p-hydroxybenzoic acid ester, undecylenic acid, thiamine lauryl sulfate, thiamine lauryl nitrate, phenol, cresol, p-chlorophenol, p-chloro-m-xylenol, p-chloro-m-cresol, thymol, phenethyl alcohol, O-phenylphenol, Irgasan CH3565, halocarban, hexachlorophene, chlorhexidine, ethanol, methanol, isopropyl alcohol, benzyl alcohol, ethylene glycol, propylene glycol, 2-phenoxyethanol, 1,2-pentanediol, zinc pyrithione, chlorobutanol, isopropylmethylphenol, a nonionic surfactant (such as polyoxyethylene lauryl ether, polyoxyethylene nonyl phenyl ether, or polyoxyethylene octyl phenyl ether), an amphoteric surfactant, an anionic surfactant (such as sodium lauryl sulfate or potassium lauroyl sarcosinate), a cationic surfactant (cetyltrimethylammonium bromide, a benzalkonium chloride, benzethonium chloride, or methylrosaniline chloride), formaldehyde, hexamine, brilliant green, malachite green, crystal violet, Germall, photosensitizer 101, photosensitizer 201, photosensitizer 401, an N-long chain acyl basic amino acid derivative and an acid addition salt thereof, zinc oxide, hinokitiol, sophora root, and propolis.

As a moisturizing agent, the capsule may contain, for example, glycerin, propylene glycol, 1,3-butylene glycol, polyethylene glycol, caprylic/capric triglyceride, glycolic acid (α-hydroxy acid), hyaluronic acid or a salt thereof, chondroitin sulfate or a salt thereof, water-soluble chitin or a derivative thereof, a chitosan derivative, pyrrolidonecarboxylic acid or a salt thereof, sodium lactate, urea, sorbitol, an amino acid or a derivative thereof (valine, leucine, isoleucine, threonine, methionine, phenylalanine, tryptophan, lysine, glycine, alanine, asparagine, glutamine, serine, cysteine, cystine, tyrosine, proline, hydroxyproline, aspartic acid, glutamic acid, hydroxylysine, arginine, ornithine, histidine, a sulfuric acid salt thereof, phosphoric acid salt thereof, nitric acid salt of thereof, or citric acid salt thereof, or pyrrolidonecarboxylic acid).

As any of various organic acids, the capsule may contain, for example, glycolic acid, citric acid, malic acid, tartaric acid, lactic acid, ferulic acid, and phytic acid.

As an agent for hair, the capsule may contain, for example, selenium disulfide, an alkylisoquinolium bromide liquid, zinc pyrithione, biphenamine, thianthol, a castoreum tincture, a ginger tincture, a capsicum tincture, quinine hydrochloride, strong ammonia water, potassium bromate, sodium bromate, and thioglycolic acid.

As a flavor, the capsule may contain, for example: a natural animal flavor, such as musk, civet, castoreum, or ambergris; a plant flavor, such as an anise essential oil, an angelica essential oil, a ylang ylang essential oil, an iris essential oil, a fennel essential oil, an orange essential oil, a cananga essential oil, a caraway essential oil, a cardamon essential oil, a guaiacwood essential oil, a cumin essential oil, a Lndera umbellata essential oil, a cinnamon bark essential oil, a cinnamon essential oil, a geranium essential oil, a copaiba balsam essential oil, a coriander essential oil, a perilla essential oil, a cedar wood essential oil, a citronella essential oil, a jasmine essential oil, a gingergrass essential oil, a Japanese cedar essential oil, a spearmint essential oil, a peppermint essential oil, a star anise essential oil, a tuberose essential oil, a clove essential oil, a neroli essential oil, a wintergreen essential oil, a tolu balsam essential oil, a patchouli essential oil, a rose essential oil, a palmarosa essential oil, a hinoki essential oil, a hiba essential oil, a sandalwood essential oil, a petitgrain essential oil, a bay essential oil, a vetiver essential oil, a bergamot essential oil, a Peru balsam essential oil, a bois de rose essential oil, a ho wood essential oil, a mandarin essential oil, an eucalyptus essential oil, a lime essential oil, a lavender essential oil, a linaloe essential oil, a lemongrass essential oil, a lemon essential oil, a rosemary essential oil, or a Japanese peppermint essential oil; and a synthetic flavor, such as coffee flavor or yogurt flavor.

In addition, the soft capsule is packed in a packing form such as bottle packing, PTP packing, or pouch, stored, and distributed.

EXAMPLES

The present invention is hereinafter specifically described by way of Examples. However, the present invention is by no means limited thereto.

The following raw materials were used.

Iota carrageenan: 40 mass % standardizing agent (sucrose) addition product (manufactured by MSC)*

Kappa carrageenan: CT-1000 (manufactured by Mitsubishi Shoji Foodtech Co., Ltd.)

Starch dispersion obtained by ultrasonically treating a starch paste solution: Fsmash (derived from waxy corn starch)

Oxidized starch: STABILOSE (manufactured by Matsutani Chemical Industry Co., Ltd.)

Heat-moisture-treated starch: Soft starch SF-930 (manufactured by Sanwa Starch Co., Ltd.)

Glycerin: Food additive grade (manufactured by Sakamoto Yakuhin Kogyo Co., Ltd.)

*Formulation amounts of "iota carrageenan" described in formulation columns of Test Examples are each an amount including the standardizing agent.

Test Examples 1 to 6 Production of Soft Capsule Using Rotary Die-Type Soft Capsule Filling Machine (1) Iota carrageenan, kappa carrageenan, a starch dispersion obtained by ultrasonically treating a starch paste solution (simply referred to as "starch dispersion"), oxidized starch, and glycerin in amounts (part(s) by mass) shown in Table 1 were stirred and dispersed in water, and then the resultant was stirred and dissolved at from 90° C. to 98° C., followed by vacuum defoaming. Soft capsules were produced from the obtained shell solution using a rotary die-type soft capsule filling machine.

Firstly, the shell solution was spread on a rotary drum in a casting apparatus to prepare a shell sheet. At this stage, [a. Evaluation of Shell Sheet Strength] and [b. Evaluation of Elongation of Shell Sheet] described below were performed.

(2) Then, two pieces of the obtained shell sheet were each fed to between a pair of rotating cylindrical dies via a lubricating roller and a deflector roll, and subjected to capsulation to form oval (football)-type soft capsules. At this stage, [c. Evaluation of Adhesive Property of Shell Sheet immediately after Capsule Formation] was performed.

(3) In addition, the obtained soft capsules were preserved for 24 hours in a desiccator adjusted to a relative humidity of 20% or less, to thereby obtain dried soft capsules. At this stage, [d. Evaluation of Elasticity of Dried Capsule], [e. Evaluation of Adhesiveness of Dried Capsule], and [f. Evaluation of Transparency of Dried Capsule] were performed.

Further, in Test Examples 1 to 4 and 6 in which capsulation was successfully performed, [g. Evaluation of Disintegrability of Dried Capsule] described below was performed. The results are shown in Table 1.

[a. Evaluation of Shell Sheet Strength]

The strength of the shell sheets was subjected to sensory evaluation by five expert panels according to the following evaluation criteria.

5: Very strong
   4: Strong
   3: Slightly weak
   2: Weak
   1: Very weak

[b. Evaluation of Elongation of Shell Sheet]

The elongation of the shell sheets was subjected to sensory evaluation by five expert panels according to the following evaluation criteria simultaneously with the evaluation of the strength of the shell sheets.

5: The shell sheet has high elongation and elasticity.
   4: The shell sheet has elongation and elasticity.
   3: The shell sheet has elongation but somewhat low elasticity.
   2: The shell sheet has little elongation and low elasticity.

1: The shell sheet has no elongation and no elasticity.

[c. Evaluation of Adhesive Property of Shell Sheet immediately after Capsule Formation]

Five expert panels pressed undried capsules with fingers and evaluated the adhesive property of the shell sheets immediately after capsule formation according to the following evaluation criteria.

5: The content solution was not leaked by strong press and was not exuded from any of the capsules after the capsules were left to stand for 24 hours.

4: The content solution was not leaked by strong press but was exuded from some of the capsules after the capsules were left to stand for 24 hours.

3: A very small amount of the content solution was leaked by strong press.

2: A small amount of the content solution was leaked by weak press.

1: The content solution was leaked by weak press.

[d. Evaluation of Elasticity of Dried Capsule]

Five expert panels pressed the capsules by fingers, and deformation of the capsules was observed to evaluate the elasticity of the capsules according to the following evaluation criteria.

5: Not deformed or returned to their original shape immediately after small deformation 4: Slightly deformed by press but returned to their original shape after some time 3: Deformed by press and returned to their original shape after a long time 2: Deformed by press and hardly returned to their original shape 1: Deformed by press and not returned to their original shape

[e. Evaluation of Adhesiveness of Dried Capsule]

The capsules in glass bottles were observed by five expert panels as to whether the capsules dropped or not when the bottles were put upside down to evaluate the adhesiveness of the capsules according to the following evaluation criteria.

5: The capsules dropped separately only by putting the glass bottles upside down.

4: The capsules dropped by putting the glass bottles upside down and mildly shaking the bottles.

3: The capsules dropped by putting the glass bottles upside down and patting the bottles.

2: The capsules dropped by putting the glass bottles upside down and strongly hitting the bottles.

1: The capsules adhered firmly to the glass bottles.

[f. Evaluation of Transparency of Dried Capsule]

The transparency of the capsules was evaluated by visual observation by five expert panels according to the following evaluation criteria.

5: Equal to the transparency of a gelatin shell

4: Almost equal to the transparency of a gelatin shell

3: Slightly poorer than the transparency of a gelatin shell

2: Nearly identical to the transparency of obscure glass

1: Equal to the transparency of obscure glass

[g. Evaluation of Disintegrability of Dried Capsule]

According to the disintegration test of Japanese Pharmacopoeia (with an auxiliary disk), the soft capsules were measured for time (minutes) taken for the oil droplet, which was the content, to leak out. The measurements were performed (n=6) and the average values were recorded.

TABLE 1

| Test Example | | | Example | | | | Comparative Example | |
|---|---|---|---|---|---|---|---|---|
| | | 1 | 2 | 3 | 4 | 5 | 6 |
| Formulation | (A) Iota carrageenan | 40 | 30 | 50 | 38 | 40 | 25 |
| | (B) Starch dispersion | 60 | 70 | 50 | 60 | — | — |
| | Kappa carrageenan | — | — | — | 2 | — | 0.5 |
| | Oxidized starch | — | — | — | — | 60 | 74.5 |
| | Glycerin | 35 | 30 | 50 | 35 | 50 | 50 |
| | Purified water | 250 | 220 | 280 | 250 | 190 | 135 |
| Evaluation of shell sheet | a. Shell sheet strength | 5 | 5 | 5 | 5 | 3 | 3 |
| | b. Elongation | 4 | 4 | 4 | 4 | 4 | 4 |
| | c. Adhesive property immediately after capsule formation | 5 | 5 | 5 | 5 | — | 4 |
| | Possibility of capsulation | Possible | Possible | Possible | Possible | Impossible | Possible |
| Evaluation of dried capsule | d. Elasticity | 4 | 4 | 4 | 4 | — | 4 |
| | e. Adhesiveness | 4 | 4 | 4 | 4 | — | 4 |
| | f. Transparency | 5 | 5 | 5 | 5 | — | 4 |
| | g. Disintegrability (minutes) | 3.0 | 3.0 | 3.0 | 3.0 | — | 5.5 |

As shown in Table 1, in Test Examples 1 to 4 in which the iota carrageenan and the starch dispersion derived from waxy corn starch were used, an excellent shell sheet strength and adhesive property at the time of capsule formation were achieved. Excellent shell performance after capsulation was also achieved. Thus, soft capsules with good quality were obtained.

In Test Example 4 in which kappa carrageenan was formulated, rapid gelation and a high yield were achieved.

On the other hand, in Test Example 5 in which the iota carrageenan and the oxidized starch were used, the adhesive property was poor and capsulation was not achieved. Further, in Test Example 6, it took long time to disintegrate the soft capsules.

Test Examples 7 and 8 Production of Soft Capsule Using Rotary Die-Type Soft Capsule Filling Machine Iota carrageenan, kappa carrageenan, a starch dispersion obtained by ultrasonically treating a starch paste solution (simply referred to as "starch dispersion"), oxidized starch, and glycerin in amounts (parts by mass) shown in Table 2 were stirred and dispersed in water, a shell solution was prepared in the same manner as in Test Examples described above, and then a self-cut-type soft capsule was produced by using a rotary die-type soft capsule filling machine.

Further, in the same manner as in Test Examples described above, [a. Evaluation of Shell Sheet Strength], [b. Evaluation of Elongation of Shell Sheet], [c. Evaluation of Adhesive Property of Shell Sheet immediately after Capsule Formation], [d. Evaluation of Elasticity of Dried Capsule], [e. Evaluation of Adhesiveness of Dried Capsule], and [f. Evaluation of Transparency of Dried Capsule] described below were performed. The results are shown in Table 2.

TABLE 2

| | Test Example | Example 7 | Comparative Example 8 |
|---|---|---|---|
| Formulation | (A) Iota carrageenan | 28 | 28 |
| | (B) Starch dispersion | 30 | — |
| | Kappa carrageenan | 2 | 2 |
| | Oxidized starch | 40 | 70 |
| | Glycerin | 45 | 45 |
| | Purified water | 150 | 150 |
| Evaluation of shell sheet | a. Shell sheet strength | 4 | 4 |
| | b. Elongation | 4 | 4 |
| | c. Adhesive property immediately after capsule formation | 5 | 3 |
| | Possibility of capsulation | Possible | Possible |
| Evaluation of dried capsule | d. Elasticity | 4 | 4 |
| | e. Adhesiveness | 4 | 4 |
| | f. Transparency | 5 | 3 |
| | g. Disintegrability (minutes) | — | — |

As shown in Table 2, in Test Example 7 in which the iota carrageenan and the starch dispersion derived from waxy corn starch were used, the soft capsules were excellent in shell sheet strength and adhesive property at the time of capsule formation, and were also excellent in shell performance after capsulation.

On the other hand, in Test Example 8 in which the iota carrageenan and the oxidized starch were used, the adhesive property was poor and the leakage of the content was observed.

Test Examples 9 to 11 Production of Soft Capsule Using Rotary Die-Type Soft Capsule Filling Machine Iota carrageenan, kappa carrageenan, a starch dispersion obtained by ultrasonically treating a starch paste solution (simply referred to as "starch dispersion"), starch subjected to heat moisture treatment in the presence of a salt (simply referred to as "heat-moisture-treated starch"), and glycerin in amounts (parts by mass) shown in Table 3 were stirred and dispersed in water, a shell solution was prepared in the same manner as in Test Examples described above, and then a soft capsule was produced by using a rotary die-type soft capsule filling machine.

Further, in the same manner as in Test Examples described above, [a. Evaluation of Shell Sheet Strength], [b. Evaluation of Elongation of Shell Sheet], [c. Evaluation of Adhesive Property of Shell Sheet immediately after Capsule Formation], [d. Evaluation of Elasticity of Dried Capsule], [e. Evaluation of Adhesiveness of Dried Capsule], [f. Evaluation of Transparency of Dried Capsule], and [g. Evaluation of Disintegrability of Dried Capsule] were performed. The results are shown in Table 3.

TABLE 3

| | | Example | | |
|---|---|---|---|---|
| | Test Example | 9 | 10 | 11 |
| Formulation | (A) Iota carrageenan | 39.9 | 29.9 | 29.9 |
| | (B) Starch dispersion | 50 | 20 | 10 |
| | Kappa carrageenan | 0.1 | 0.1 | 0.1 |
| | Heat-moisture-treated starch | 10 | 50 | 60 |
| | Glycerin | 50 | 50 | 50 |
| | Purified water | 200 | 165 | 160 |
| Evaluation of shell sheet | a. Shell sheet strength | 5 | 5 | 5 |
| | b. Elongation | 4 | 4 | 4 |
| | c. Adhesive property immediately after capsule formation | 5 | 5 | 5 |
| | Possibility of capsulation | Possible | Possible | Possible |
| Evaluation of dried capsule | d. Elasticity | 4 | 4 | 4 |
| | e. Adhesiveness | 4 | 4 | 4 |
| | f. Transparency | 5 | 5 | 5 |
| | g. Disintegrability (minutes) | 3.0 | 3.0 | 3.0 |

As shown in Table 3, in Test Examples 9 to 11 in which the iota carrageenan and the starch dispersion derived from waxy corn starch were used, the soft capsules were excellent in shell sheet strength and adhesive property at the time of capsule formation, and were also excellent in shell performance after capsulation.

The invention claimed is:

1. A soft capsule shell, comprising:
   (A) 25 mass % to 55 mass % with respect to a total amount of solid components of iota carrageenan; and
   (B) 10 mass % to 75 mass % with respect to a total amount of solid components of a starch dispersion obtained by ultrasonically treating a starch paste solution.

2. The soft capsule shell according to claim 1, further comprising a plasticizer.

3. The soft capsule shell according to claim 1, wherein a content mass ratio (A):(B) between (A) the iota carrageenan and (B) the starch dispersion obtained by ultrasonically treating a starch paste solution with respect to a total amount of solid components is from 1:0.3 to 1:3.

4. The soft capsule shell according to claim 1, wherein (B) the starch dispersion obtained by ultrasonically treating a starch paste solution comprises a starch dispersion derived from waxy corn starch.

5. The soft capsule shell according to claim 4, wherein the waxy corn starch is a chemically unmodified starch.

6. The soft capsule shell according to claim 1, further comprising kappa carrageenan.

7. The soft capsule shell according to claim 6, wherein a content of the kappa carrageenan is from 0.1 mass % to 3.5 mass % with respect to a total amount of solid components.

8. A soft capsule, comprising the soft capsule shell of claim 1.

9. The soft capsule shell according to claim 1, wherein (A) is present in an amount of 30 mass % to 50 mass % with respect to the total amount of the solid components.

10. The soft capsule shell according to claim 1, wherein (A) is present in an amount of 35 mass % to 45 mass % with respect to the total amount of the solid components.

11. The soft capsule shell according to claim 1, wherein (B) is present in an amount of 20 mass % to 75 mass % with respect to the total amount of the solid components.

12. The soft capsule shell according to claim 1, wherein (B) is present in an amount of 28 mass % to 75 mass % with respect to the total amount of the solid components.

13. The soft capsule shell according to claim 1, wherein (B) is present in an amount of 45 mass % to 75 mass % with respect to the total amount of the solid components.

14. The soft capsule shell according to claim 1, wherein (B) is present in an amount of 50 mass % to 75 mass % with respect to the total amount of the solid components.

15. The soft capsule shell according to claim 1, wherein (B) is present in an amount of 55 mass % to 65 mass % with respect to the total amount of the solid components.

16. The soft capsule shell according to claim 1, wherein a content mass ratio (A):(B) between (A) the iota carrageenan and (B) the starch dispersion obtained by ultrasonically treating a starch paste solution with respect to a total amount of solid components is from 1:1 to 1:2.3.

* * * * *